United States Patent
Wakabayashi et al.

(10) Patent No.: US 7,572,775 B2
(45) Date of Patent: Aug. 11, 2009

(54) METHOD OF INHIBITING INTESTINAL POLYPS

(75) Inventors: Keiji Wakabayashi, Meguro-ku (JP); Michihiro Mutoh, Setagaya-ku (JP)

(73) Assignees: Japan as Represented by Director General of Agency of National Cancer Center, Tokyo (JP); Otsuka Pharmaceutical Factory, Inc., Tokushima (JP)

( * ) Notice: Subject to any disclaimer, the term of this patent is extended or adjusted under 35 U.S.C. 154(b) by 68 days.

(21) Appl. No.: 11/665,151

(22) PCT Filed: Sep. 30, 2005

(86) PCT No.: PCT/JP2005/018100

§ 371 (c)(1),
(2), (4) Date: Apr. 12, 2007

(87) PCT Pub. No.: WO2006/040940

PCT Pub. Date: Apr. 20, 2006

(65) Prior Publication Data

US 2008/0139516 A1    Jun. 12, 2008

(30) Foreign Application Priority Data

Oct. 13, 2004   (JP)   ............ 2004-299217

(51) Int. Cl.
*A61K 31/662* (2006.01)
(52) U.S. Cl. ..................... 514/113
(58) Field of Classification Search .......... 514/113
See application file for complete search history.

(56) References Cited

FOREIGN PATENT DOCUMENTS

| JP | 61151199 A | 7/1986 |
|---|---|---|
| JP | 03068592 A | 3/1991 |
| JP | 10265387 A | 10/1998 |
| JP | 11302178 A | 11/1999 |
| JP | 2001064172 A | 3/2001 |

OTHER PUBLICATIONS

Katsuhisa Yamada et al., "Relation of Serum Total Cholesterol, Serum Triglycerides and Fasting Plasma Glucose to Colorectal Carcinoma in situ", International Journal of Epidemiology, Oct. 1998, pp. 794-798, vol. 27, No. 5, International Epidemiological Association, Great Britain.

Banke Agarwal, et al., "Lovastatin Augments Sulindac-Induced Apoptosis in Colon Cancer Cells and Potentiates Chemopreventive Effects of Sulindac", Gastroenterology, Oct. 1999, pp. 838-847, vol. 117, No. 4, The American Gastroenterological Association, New York, New York.

Naoko Niho et al., "Concomitant Suppression of Hyperlipidemia and Intestinal Polyp Formation in Apc-deficient Mice by Peroxisome Proliferator-activated Receptor Ligands", Cancer Research, Sep. 15, 2003, pp. 6090-6095, vol. 63, National Cancer Center Research Institute, Tokyo, Japan.

*Primary Examiner*—Phyllis G. Spivack
(74) *Attorney, Agent, or Firm*—Sughrue Mion, PLLC

(57) ABSTRACT

The present invention provides a method for reducing the occurrence and progress of intestinal polyps that may develop into colon cancer, and a carboxylic acid amide compound as an active component to reduce intestinal polyps, represented by the following Formula:

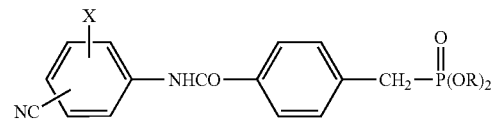

wherein R is a lower alkyl group and X is a halogen an example being 4-diethoxyphosphinoylmethyl-N-(4-bromo-2-cyanophenyl) benzamide.

2 Claims, 1 Drawing Sheet

[FIGURE 1]
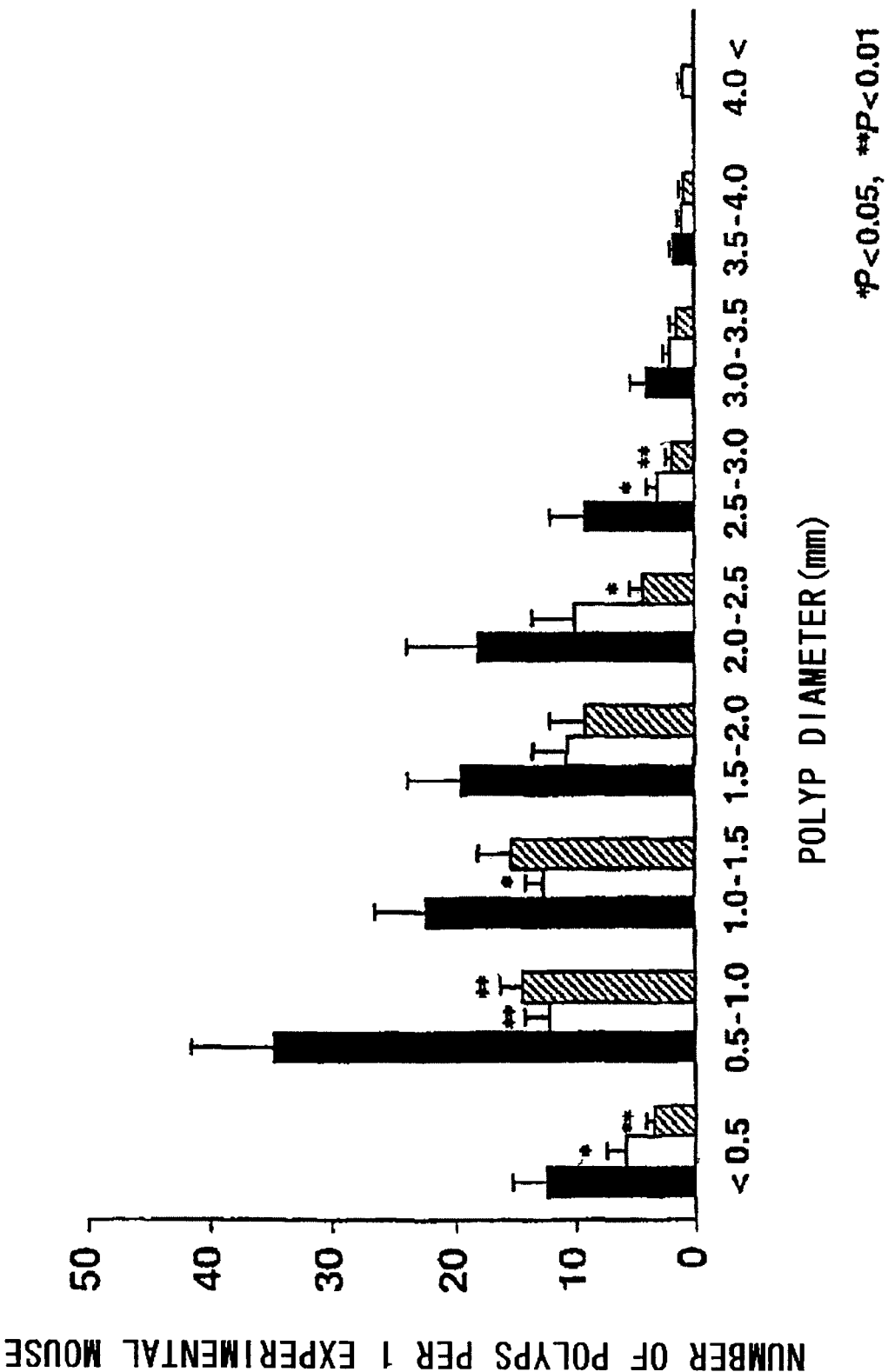

METHOD OF INHIBITING INTESTINAL POLYPS

This application is a 371 of PCT/JP2005/018100, filed Sep. 30, 2005; the disclosure of which is incorporated herein by reference.

TECHNICAL FIELD

The present invention relates to an intestinal polyp suppressor

BACKGROUND ART

Intestinal polyps are protruding lesions of the intestinal epithelium, occurring chronically in the intestines. The number of polyps ranges widely from 1 to 100 or more depending on the underlying condition. Pathologically speaking they include a variety of lesions ranging from benign neoplastic lesions to malignant neoplastic lesions, including hyperplastic lesions, dysplastic lesions, adenomas and adenocarcinomas. Particular worrisome from a clinical perspective is the fact that when a lesion exceeds 1.5 cm in size it may turn malignant, eventually becoming the base of a colonic tumor. Consequently, intestinal polyps are removed endoscopically by polypectomy or the like using a colonoscope. However, endoscopic surgery using a colonoscope is time-consuming and burdensome for the patient, and cannot generally be called an entirely satisfactory treatment. Moreover, patients with familial adenomatous polyposis (FAP) or adenomatous polyposis coli (APC), a high-risk group for colon cancer, commonly suffer from 100 or more intestinal polyps, and these polyps can become cancerous. Consequently, such patients may have no choice but to undergo total colonectomies while still young in order to prevent intestinal cancer.

At present the only known treatment for intestinal polyps is the endoscopic surgery discussed above, and no drugs are known that are aimed at suppression. That is, no drugs are known for treatment and/or prevention (suppression of occurrence). Research has just begun on such drugs. There is demand in the art for a drug that would be effective in inhibiting the occurrence of such intestinal polyps.

The inventors have long dedicated themselves to research aimed at providing effective drug components. In the process of this research, we discovered previously that a series of carboxylic acid amide compounds are useful as anti-inflammatory drugs and calcium antagonists, and perfected an invention based on this finding (Japanese Patent Application Laid-open No. S61-151199). We later discovered that another group of carboxylic acid amide compounds with a similar framework have excellent lipid-lowering ability and are useful in the prevention and treatment of hyperlipidemia, and perfected an invention based on this finding (Patent #2584336, Specifications). We also discovered within this group of compounds a new compound that acts on urinary protein excretion and is effective for treating nephritis, and perfected an invention based on this finding (Japanese Patent Application Laid-open No. H10-265387). In addition, we discovered that this compound which is useful as a nephritis treatment agent also has a separate effect of lowering neutral lipids (triglycerides, TG), total cholesterol and the like, in the liver, and is useful as an agent for preventing and treating fatty liver (Japanese Patent Application Laid-open No. H11-302178).

DISCLOSURE OF THE INVENTION

It is an object of the present invention to provide a compound that is useful for suppressing intestinal polyps. More specifically, the present invention provides a medicine (drug) capable of preventing the occurrence of intestinal polyps, arresting their progress, and providing a therapeutic effect. It is another object of the present invention to provide a method of suppressing intestinal polyps using an intestinal polyp suppressor comprising this compound.

The inventors in this case discovered for the first time as a result of further research aimed at achieving these objects that specific previously-developed carboxylic acid amide compounds, and 4-diethoxyphosphinoylmethyl-N-(4-bromo-2-cyanophenyl)benzamide in particular, have an intestinal-polyp suppressing effect that meets the aforementioned object. The present invention was perfected as a result of further research based on this finding.

The present invention provides an intestinal polyp suppressors described in Items 1 and 2 below, methods for suppressing the intestinal polyp described in Items 3 and 4, and the use of a carboxylic acid amide compound for the manufacture of an intestinal polyp suppressor or as an intestinal polyp suppressor as described in Items 5 to 8.

Item 1. An intestinal polyp suppressor, containing an effective amount of a carboxylic acid amide compound represented by the following General Formula:

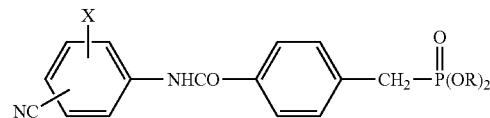

(wherein R is a lower alkyl group and X is a halogen) together with pharmaceutically acceptable carriers.

Item 2. An intestinal polyp suppressor according to Item 1, wherein the carboxylic acid amide compound is 4-diethoxyphosphinoylmethyl-N-(4-bromo-2-cyanophenyl)benzamide.

Item 3. A method for suppressing the occurrence and progress of intestinal polyps in patients with intestinal polyps, patients at high risk of intestinal polyps and patients at high risk of colon cancer, comprising administering to those patients an effective amount of a carboxylic acid amide compound according to Item 1.

Item 4. A method according to Item 3, wherein a carboxylic acid amide compound is 4-diethoxyphosphinoylmethyl-N-(4-bromo-2-cyanophenyl)benzamide.

Item 5. Use of a carboxylic acid amide compound according to Item 1 for the manufacture of an intestinal polyp suppressor.

Item 6. Use of 4-diethoxyphosphinoylmethyl-N-(4-bromo-2-cyanophenyl)benzamide for the manufacture of an intestinal polyp suppressor.

Item 7. Use of the intestinal polyp suppressor according to 1 for suppressing intestinal polyps.

Item 8. Use of 4-diethoxyphosphinoylmethyl-N-(4-bromo-2-cyanophenyl)benzamide for suppressing intestinal polyps.

The intestinal polyp suppressor of the present invention provides excellent intestinal polyp-suppressing effects. That is, this suppressor prevents the occurrence of intestinal polyps (preventative effect) when administered to patients with intestinal polyps or people at high risk of developing intestinal polyps. Moreover, it can inhibit the progress of existing intestinal polyps and shrink lesions (therapeutic effect) when administered to patients with intestinal polyps. The intestinal polyp suppressor of the present invention is also desirable as a drug because it has no serious side effects.

BRIEF DESCRIPTION OF THE DRAWINGS

FIG. 1 shows the results of the intestinal polyp suppression test described in Example 2.

BEST MODE FOR CARRYING OUT THE INVENTION

In the intestinal polyp suppressor of the present invention, the carboxylic acid amide compound, that is the active component, is the compound represented by General Formula (1) above (this compound is sometimes called "Compound (1)" below).

In the formula, the lower alkyl group represented by R may be a straight-chain or branched-chain alkyl group with 1 to 6 carbon atoms. Examples include methyl, ethyl, n-propyl, isopropyl, n-butyl, isobutyl, tert-butyl, n-pentyl and n-hexyl groups and the like. The halogen atom represented by X may be fluorine, chlorine, bromine or iodine.

Of the carboxylic acid amide compounds represented by General Formula (1) above, 4-diethoxyphosphinoylmethyl-N-(4-bromo-2-cyanophenyl)benzamide is preferred for its superior effects.

Compound (1) was previously developed by the inventors in this case (see Japanese Patent Application Laid-open No. S61-151199, Japanese Patent No. 2584336 and Japanese Patent Applications Laid-open Nos. H10-265387 and H11-302178), and can be manufactured by the methods described in these documents. More specifically, it can be manufactured by reacting a carboxylic acid halide such as 4-diethoxy-phosphinoylmethyl-benzchloride with 4-bromo-2-cyanophenylamine. The details of this reaction are described in the documents listed above, and the descriptions of these documents are incorporated into the present specification.

None of the documents listed above describe that this Compound (1) is effective at suppressing intestinal polyps. In the past, no association was known between an intestinal polyp suppression effect and the pharmacological effects described in these documents, such as calcium antagonism, lipid lowering, and effects against urinary protein excretion.

Compound (1) has excellent intestinal polyp suppressing effects, and moreover has the highly desirable property of having no serious side effects.

It is a requirement that the intestinal polyp suppressor of the present invention contain Compound (1) as an effective component, and normally it is prepared in a variety of formulations using the compound together with pharmaceutically acceptable carriers commonly used in the art according to the method of administration.

Examples of pharmaceutically acceptable carriers include various diluents and solvents, fillers, extenders, binders, suspension agents, disintegrants, surfactants, lubricants, excipients, humectants and the like that are commonly used in the art. One of these may be used alone, or two or more may be used in combination according to the formulation being prepared. One or more solubilizers, buffers, preservatives, colorants, perfumes, flavorings or the like that are commonly used in the pharmaceutical art may also be added to the preparation as necessary.

The formulation and administration route of the medicine of the present invention are not particularly limited and can be determined appropriately. Examples of formulations include tablets, capsules, granules, pills, syrups, liquids, emulsions, suspensions and other orally administered forms as well as injections (subcutaneous, intravenous., intramuscular, intraperitoneal, etc.) and other parenterally administered forms. The orally administered forms are administered orally. The injections and other parenterally administered forms can be administered intravenously either alone or in combination with commonly used replenishers such as glucose, amino acids and the like, or can be administered alone either intramuscularly, subcutaneously or intraperitoneally.

The medicine of the present invention is prepared by methods ordinarily used in the art of such preparations using pharmaceutically acceptable carriers. In the case of an orally administered form such as tablets, capsules, granules, pills or the like, the medicine can be prepared by ordinary methods using excipients such as sucrose, lactose, glucose, starch and mannitol; binders such as syrup, gum arabic, sorbitol, tragacanth, methyl cellulose and polyvinylpyrrolidone; disintegrators such as starch, carboxymethyl cellulose or its calcium salt, microcrystalline cellulose and polyethylene glycol; lubricants such as talc, magnesium stearate, calcium stearate and silica; and humectants such as sodium laurate, glycerol and the like.

An injection, liquid, emulsion, suspension or syrup can be prepared by ordinary methods using as necessary such solvents as ethyl alcohol, isopropyl alcohol, propylene glycol, 1,3-butylene glycol, polyethylene glycol and sesame seed oil for dissolving the active component; surfactants such as sorbitan fatty acid ester, polyoxyethylene sorbitan fatty acid ester, polyoxyethylene fatty acid ester, hydrogenated castor oil polyoxyethylene ether and lecithin; suspending agents such as sodium carboxymethyl cellulose, methyl cellulose and other celluloses compound and tragacanth, gum arabic and the like; and preservatives such as paraoxybenzoic acid esters, benzalkonium chloride, sorbitan acid salts and the like.

The amount of an active component compound to be contained in the medicine of the present invention can be selected appropriately from a wide range. Usually, it may be selected from the range at which it constitutes 1 to 70 wt % of the preparation.

The administered amount of the medicine of the present invention may be determined at will depending on the formulation, administration route, age and weight of the patient, severity of the condition and the like, without any particular limitations. In the case of an orally administered form, the amount of the active component contained in each formulation is usually set so that about 0.05 to 80 mg or preferably about 0.1 to 50 mg per 1 kg of adult body weight is administered per day, but this can be increased or decreased appropriately as necessary. In the case of a parenterally administered form, the dosage may be determined appropriately so as to be consistent with the administered amount of the orally administered form.

The intestinal polyp suppressor of the present invention can inhibit the occurrence and progress of colon polyps when administered to patients suffering from intestinal polyps and people at high risk of developing intestinal polyps, including typically familial adenomatous polyposis (FAP) patients and their relatives for example. In particular, because cancers are likely to originate from colon polyps larger than 1.5 cm, the intestinal polyp suppressor of the present invention can be applied effectively not only to FAP patients, who are in a high risk group for colon cancer, but even to patients with sporadic colon polyps if the polyps are large, as well as to people with a family history of colon cancer (FAP carriers).

The present invention provides a method for suppressing intestinal polyps comprising administering an amount of compound (1) sufficient to suppress intestinal polyps to an intestinal polyp patient, a patient in a high-risk group for intestinal polyps or a patient in a high-risk group for colon cancer.

Moreover, the present invention also encompasses the use of Compound (1) for the manufacture an intestinal polyp suppressor, and the use of the intestinal polyp suppressor of the present invention for suppressing intestinal polyps.

EXAMPLES

To better explain the present invention, Example 1 is given below as a prescriptive example of the intestinal polyp suppressor of the present invention.

Example 1

(1) Preparation of Tablets

Tablets (1000 tablets) each containing 250 mg of the active component compound 4-diethoxyphosphinoylmethyl-N-(4-bromo-2-cyanophenyl)benzamide (hereunder "Compound A") were prepared according to the following formulation.

| Component | Amount (g) |
| --- | --- |
| Compound A | 250 |
| Lactose (per Japanese Pharmacopoeia) | 33.3 |
| Corn starch (per Japanese Pharmacopoeia) | 16.4 |
| Carboxymethyl cellulose calcium (per Japanese Pharmacopoeia) | 12.8 |
| Methyl cellulose (per Japanese Pharmacopoeia) | 6.0 |
| Magnesium stearate (per Japanese Pharmacopoeia) | 1.5 |
| Total | 320 |

The Compound A, lactose, corn starch and carboxymethyl cellulose calcium were thoroughly mixed according to this formulation, and the mixture was granulated with an aqueous methyl cellulose solution, passed through a #24 mesh, mixed with magnesium stearate and pressed into tablets.

(2) Preparation of Capsules

Hard gelatin capsules (1000 capsules) each containing 250 mg of Compound A were prepared according to the following formulation.

| Component | Amount (g) |
| --- | --- |
| Compound A | 250 |
| Crystal cellulose (per Japanese Pharmacopoeia) | 30 |
| Corn starch (per Japanese Pharmacopoeia) | 17 |
| Talc (per Japanese Pharmacopoeia) | 2 |
| Magnesium stearate (per Japanese Pharmacopoeia) | 1 |
| Total | 300 |

The various components were finely powdered and thoroughly mixed so as to obtain a uniform mixture according to this formulation, and then packed into oral-administration gelatin capsules of the desired dimensions to obtain capsules.

(3) Preparation of Granules

Granules (1000 g) containing 500 mg of Compound A per gram were prepared according to the following formulation.

| Component | Amount (g) |
| --- | --- |
| Compound A | 500 |
| Corn Starch (per Japanese Pharmacopoeia) | 250 |
| Lactose (per Japanese Pharmacopoeia) | 100 |
| Crystal cellulose (per Japanese Pharmacopoeia) | 100 |
| Carboxymethyl cellulose calcium (per Japanese Pharmacopoeia) | 40 |
| Hydroxypropyl cellulose (per Japanese Pharmacopoeia) | 10 |
| Total | 1000 |

The Compound A, corn starch, lactose, crystal cellulose and carboxymethyl cellulose calcium were mixed according to this formulation, and an aqueous hydroxypropyl cellulose solution was added and kneaded into the mixture, which was then granulated in an extrusion granulator and dried for 2 hours at 50° C. to obtain the target granules.

An example of a pharmacological test performed on the active component compound of the intestinal polyp suppressor of the present invention is given below as Example 2.

Example 2

The intestinal polyp-suppressing effects of the active component compound of the present invention were investigated as follows.

(1) Experimental Animals

The experimental animals were male Min mice of a familial adenomatous polyposis model (Apc (Adenomatous polyposis coli) gene deficient mice, C57BL/6-ApcMin/+, Jackson Laboratory, Bar Harbor, Me.). These mice were purchased at age 5 weeks, and acclimatized for 2 weeks to laboratory conditions (24±2° C., humidity 55%, 12 hours light/12 hours dark cycle, free access to feed and water) before being used in the tests. The feed was "AIN-76A" basic feed (Clea Japan).

Wild-type C54BL6J mice (from the same source) were subjected to the same test as a control.

(2) Experimental Medicine

Compound A was used as the experimental medicine. The compound was mixed to a specific concentration (400 ppm or 800 ppm) with the AIN-76A basic feed for use in the tests.

(3) Experimental Methods

Feed comprising a specific amount of the experimental medicine mixed to a specific concentration with basic feed (AIN-76A) was administered to the experimental group mice (2 groups of 10 mice) and comparison group mice (1 group of 10 mice) for 13 weeks from age 7 weeks to age 20 weeks (natural feeding). When death was confirmed during the experiment, however, administration was naturally discontinued.

A group of 10 mice receiving basic feed (AIN-76A) without the experimental medicine added for the same length of time was set up as a control group (experimental drug non-administration group).

(4) Intestinal Polyp Assay 13 weeks after the start of the experiment the mice in all groups (excluding those which had died) were euthanized, and an intestinal polyp assay was performed as follows.

3 mice died in the control group and 2 in the experimental group receiving feed mixed with 400 ppm of the experimental medicine, with death being due to bleeding from polyps in all cases.

The intestines were removed from the mice in all groups, placed in phosphate buffer containing 10% formalin, and then separated into four parts: (1) the colon, (2) the proximal part of the small intestine (about 4 cm long beginning at the pylorus), (3) the central part of the small intestine (the center of the remaining half of the small intestine) and (4) the distal part of the small intestine (the distal part of the remaining half of the small intestine). Each part was opened longitudinally, and fixed flat between sheets of filter paper in phosphate buffer containing 10% formalin.

The number and size of polyps and their distribution in the intestines were counted, measured and evaluated under a stereoscopic microscope. These methods are described in the literature reference(Watanabe, K. et al., "Role of the prostaglandin E receptor subtype EP1 in colon carcinogenesis", Cancer Res., 59, 5093-6 (1999)).

(5) Results

The results are shown in Table 1 and FIG. 1.

Table 1 shows results for number of polyps per mouse in each group (average ±SE).

TABLE 1

| Dose (ppm) | Mice | Number of polyps/mouse |  |  |  |  |
|---|---|---|---|---|---|---|
|  |  | Small intestine |  |  |  |  |
|  |  | Proximal | Central | Distal | Colon | Total |
| 0 | 7/10 | 23.1 ± 4.2[a] | 37.1 ± 11.1 | 60.4 ± 12.2 | 1.0 ± 0.2 | 121.7 ± 26.0 |
| 400 | 8/10 | 8.5 ± 1.4 (37)[d] | 16.1 ± 3.8 (43) | 33.0 ± 6.5 (55) | 0.4 ± 0.2 (38)[c] | 58.0 ± 10.8 (48)[c] |
| 800 | 10/10 | 5.9 ± 1.0 (26)[d] | 13.8 ± 2.6 (37)[c] | 30.5 ± 5.0 (51)[c] | 0.3 ± 0.2 (30)[c] | 50.5 ± 7.8 (42)[c] |

The numbers in brackets in the table indicate percentage of the result for the 0 dose (control) group.
The superscript letters indicate the following:
[a]Mean ± SD
[c]Significantly different (p < 0.05) from results for 0 dose (control) group
[d]Significantly different (p < 0.01) from results for 0 dose (control) group.

FIG. 1 is a graph showing the association between polyp number and diameter, with the number of polyps per experimental mouse from Table 1 plotted on the vertical axis and polyp diameter (mm) on the horizontal axis. In FIG. 1, a black bar indicates results for the control group (test medicine non-administration group), a white bar indicates results for the 400 ppm group (group given feed mixed with 400 ppm of test medicine), and a shaded bar indicates results for the 800 ppm group (group given feed mixed with 800 ppm of test medicine). The two asterisks in the FIGURE indicate the following:

*: Significantly different (p<0.05) from control group according to Dunnett's multiple comparison test
**: Significantly different (p<0.01) from control group according to Dunnett's multiple comparison test (6) Discussion From the results shown in Table 1 and FIG. 1, it is clear that the Compound A used as the active component in the present invention has an excellent polyp suppression effect at a dosage of either 400 ppm or 800 ppm.

More specifically, at both dosages Compound A can have the effect of dose-dependently reducing the number of polyps. In particular, a reduction in the number of polyps of all sizes was seen due to administration of Compound A. This suggests that Compound A not only delays the time of polyp onset but also acts to inhibit polyp growth. Because Apc gene deficient mice were used in this test, the effect on the initiation period (period when DNA damage occurs) of human tumor onset could not be evaluated, but it appears that Compound A may be effective during the promotion period (period during which tumors progress). In particular, suppressing the number of large polyps (3 mm or larger) has the effect of reducing the number of polyps closer to the original site of carcinogenesis, suggesting that Compound A is also effective at suppressing the progress of tumor malignancy. Like common candidate drugs for cancer prevention, Compound A has the effect of suppressing tumor enlargement, and could also be useful as a therapeutic cancer drug.

From the results shown in Table 1 and FIG. 1, it is considered that the Compound A has the effect of suppressing both the occurrence and growth of polyps.

INDUSTRIAL APPLICABILITY

The intestinal polyp suppressor of the present invention is useful in the drug field because it can prevent the occurrence and inhibit the development of intestinal polyps when administered, as well as provide therapeutic effects.

What is claimed is:

1. A method for reducing or inhibiting the occurrence and progress of intestinal polyps comprising administering to a patient in need thereof an effective amount of a carboxylic acid amide compound represented by the following Formula:

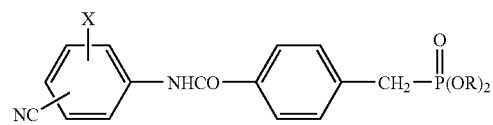

wherein R is a lower alkyl group and X is a halogen atom.

2. The method according to claim 1, wherein the carboxylic acid amide compound is 4-diethoxyphosphinoylmethyl-N-(4-bromo-2-cyanophenyl)benzamide.

* * * * *